United States Patent [19]

Demaiziere et al.

[11] Patent Number: 5,705,720
[45] Date of Patent: Jan. 6, 1998

[54] CONTINUOUS PROCESS FOR CRACKING 1,2-DICHLOROETHANE

[75] Inventors: Claude Demaiziere, Martigues; Jean Lesparre, Volonne; Yves Correia, Chateau-Arnoux, all of France

[73] Assignee: Atochem, Puteaux, France

[21] Appl. No.: 475,832

[22] Filed: Jun. 7, 1995

Related U.S. Application Data

[63] Continuation of Ser. No. 40,354, Mar. 30, 1993, which is a continuation of Ser. No. 925,897, Aug. 7, 1992, abandoned, which is a continuation of Ser. No. 653,472, Feb. 11, 1991, abandoned, which is a continuation of Ser. No. 427,913, Oct. 24, 1989, abandoned, which is a continuation of Ser. No. 318,080, Feb. 28, 1989, abandoned, which is a continuation of Ser. No. 97,415, Sep. 15, 1987, abandoned, which is a continuation of Ser. No. 841,200, Mar. 19, 1986, abandoned.

[30] Foreign Application Priority Data

Mar. 20, 1985 [FR] France ................................. 85 04101

[51] Int. Cl.$^6$ ................................................. C07C 17/25
[52] U.S. Cl. ........................... 570/226; 570/229; 570/230
[58] Field of Search ................................... 570/226, 229, 570/230

[56] References Cited

U.S. PATENT DOCUMENTS 3,222,407 12/1965 Leach et al. .
3,290,399 12/1966 Branconier et al. .
3,476,955 11/1969 Krokeler et al. .
4,590,318 5/1986 Longhini et al. .
4,665,243 5/1987 Burks .

FOREIGN PATENT DOCUMENTS 1306945 9/1962 France .
1210800 2/1966 Germany .
16404 4/1974 Japan .
573532 11/1945 United Kingdom .

OTHER PUBLICATIONS

Webster Third New International Dictionary, Unabridged, 1963, p.350.
Holbrook et al, *J. Chem. Soc.* (B), pp. 577–582 (1971).
J-A-50/062,911.
Kolesnikov et al, *J. Appl. Chem. USSR*, pp. 383–386 (1985).

*Primary Examiner*—Charles T. Jordan
*Assistant Examiner*—Anthony R. Chi
*Attorney, Agent, or Firm*—Burns, Doane, Swecker & Mathis, L.L.P.

[57] ABSTRACT

A thermal process for cracking 1,2-dichloroethane to form vinyl chloride comprising heating 1,2-dichloroethane in a reaction zone at a temperature between 300° and 650° C. under an absolute pressure between 1 and 40 bars; said heating being conducted in the presence of hydrochloric acid.

11 Claims, No Drawings

CONTINUOUS PROCESS FOR CRACKING 1,2-DICHLOROETHANE

This application is a continuation of application Ser. No. 08/040,354, filed Mar. 30, 1993, which is a continuation of application Ser. No. 07/925,897, filed Aug. 7, 1992 (now abandoned), which is a continuation of Ser. No. 07/653,472, filed Feb. 11, 1991 (now abandoned), which is a continuation of Ser. No. 07/427,913, filed Oct. 24, 1989 (now abandoned), which is a continuation of Ser. No. 07/318,080, filed Feb. 28, 1989 (now abandoned), which is a continuation of Ser. No. 07/097,415, filed Sep. 15, 1987 (now abandoned), which is a continuation of Ser. No. 06/841,200, filed Mar. 19, 1986 (now abandoned).

BACKGROUND OF THE INVENTION

The invention relates to a continuous process for cracking 1,2-dichloroethane to vinyl chloride.

The cracking processes consist in heating 1,2-dichloroethane vapor to a temperature of the order of 300° to 650° C. at a pressure of 8 to 40 bars. To restrict the proportion of heavy products formed during this operation (chlorinated hydrocarbons containing at least 4 carbon atoms and capable of giving rise to carbonaceous particles which can foul the cracking furnace), the conversion (molar ratio of cracked 1,2-dichloroethane to 1,2-dichloroethane introduced) can be between 50 and 70% (French Patent 1,302,458) and more precisely between 55 and 65% (French Patent 1,491,946). In fact, this conversion is usually limited to 55% in industrial applications (Techniques de l'Ingenier 9-1984).

In French Patent 721,808 it has been proposed to conduct the cracking reaction in the presence of steam or of a diluent such as hydrochloric acid, nitrogen or carbon dioxide. According to this patent, which is aimed at producing vinyl chloride and acetylene simultaneously, the operation is carried out at a temperature of at least 800° C. and preferably between 800° and 1,000° C., steam being the recommended diluent.

French Patent 1,306,945 proposes to limit the conversion or, when a high conversion is desired, to add a diluent such as hydrochloric acid. However, the process described in this French Patent 1,306,945 is exclusively concerned with a process for catalytic dissociation of 1,2-dichloroethane. This process, which makes use of a solid catalyst, is generally employed at a temperature between 160° and 350° C., and under absolute pressure which does not exceed 2.5 atmospheres. According to this process, the decrease in the concentration of vinyl chloride is produced by an addition of the same volume of hydrochloric acid.

SUMMARY OF THE INVENTION

The invention provides a thermal cracking process which can be employed at a temperature well below 800° C., and in which the conversion can reach 95% or even higher without risk to the equipment or to the profitability of the process.

The process according to the invention comprises the thermal cracking of 1,2-dichloroethane at a temperature between about 300° and 650° C. under an absolute pressure between 1 and 40 bars; the cracking being conducted in the presence of hydrochloric acid.

DETAILED DESCRIPTION

More precisely, the invention relates to a process such as defined above, in which the molar ratio of hydrochloric acid to 1,2-dichloroethane is between 0.1 and 1.8 and is preferably between 0.2 and 1.5. This process is preferably employed at a temperature between 350° and 550° C. and/or under an absolute pressure between 1 and 25 bars.

According to an alternative form of this process, one or more substances capable of giving free radicals, such as $Cl_2$, $CCl_4$, $C_2Cl_6$; this list not being restrictive, are added to the stream which enters the furnace (1,2-dichloroethane and HCl). In general, when such additives are used, the molar ratio of additive to 1,2-dichloroethane can attain $10^{-2}$ and is preferably between $10^{-4}$ and $5 \times 10^{-3}$.

This process can be carried out in equipment which is generally used for cracking and especially in multitube furnaces in which the efficiency of this process is particularly noticeable in view of the sensitivity of these reactors to fouling.

The use of this process makes it possible to operate at a very high conversion which can exceed 95%. It is remarkable to find that, despite a conversion as high as this, the furnaces can be used for very long periods without any carbonaceous deposits being observed on the walls of these furnaces.

The invention will be further described in connection with the following examples which are set forth for purposes of illustration only.

In these examples "D 12" stands for 1,2-dichloroethane and "VC" stands for vinyl chloride.

EXAMPLE 1

2.5 moles/hour of D 12 and 1.61 moles/hour of HCl are introduced into a reactor consisting of an Inconel coil 8 mm in bore and 3.48 m long, maintained at 480° C. by means of a lead bath. The pressure in the reactor is atmospheric. After absorption of HCl, the stream leaving the reactor has the composition given in the table below. The cracking ratio or conversion of D 12 is 97.5 mol %.

As a comparative example, and with the aim of producing the same concentration of vinyl chloride at the gas outlet, a test is carried out in which 5.77 moles/hour of D 12 are introduced under the same temperature and pressure conditions as in the above test; the stream leaving the reactor has the composition which is given in the table below, and the conversion of D 12 is 56.2 mol %. The high output of "condensed solvents", consisting essentially of uncracked D 12, is noted.

It is noted that after 10 hours continuous running, the operation of the process according to the invention is still correct. In a comparative test carried out with 3 moles/hour of D 12 to produce a cracking ratio of 96–98%, the furnace is completely blocked by heavy impurities after one hour's running.

|  | Example 1 | Control |
|---|---|---|
| Vented gas Composition | | |
| Output (mol/hour) | 2.44 | 3.24 |
| $C_2H_2$ (mol %) | 0.0635 | 0.2370 |
| $C_2H_4$ (mol %) | 0.0215 | 0.0320 |
| VC (mol %) | 98.3950 | 98.6580 |
| Chloroprenes | 0.2750 | — |
| $CHCl_3$ (mol %) | 0.8774 | 2.0730 |

-continued

| | Example 1 | Control |
|---|---|---|
| Condensed solvent Composition | | |
| Output (g/h) | 15.4 | 231.7 |
| Light impurities* (weight %) | 1.77 | 1.03 |
| D 12 (weight %) | 93.6510 | 93.3610 |
| Heavy impurities** (weight %) | 1.56 | 0.14 |

*Lights = 1,1,1-trichloroethane, $CHCl_3$, chloroprene, $CCl_4$, trichloroethylene in particular
**Heavies = chlorinated $C_3$, $C_4$, $C_6$ derivatives in particular.

EXAMPLES 2 TO 6

The test of Example 1 is repeated under the same operating conditions and the results collated in the following table are observed:

| Examples | 2 | 3 | 4 | 5 | 6 |
|---|---|---|---|---|---|
| Furnace temperature °C. | 490 | 470 | 450 | 490 | 490 |
| Feed: | | | | | |
| D 12 (mol/h) | 2.4 | 5 | 4 | 4.35 | 4.35 |
| HCl (mol/h) | 3.6 | 7.5 | 6 | 1.65 | 1.65 |
| $Cl_2$ (mg/kg D 12) | — | 5200 | 5600 | 5200 | 1580 |
| Cracking ratio based on D 12 (%) | 75.1 | 85.4 | 85.7 | 90.5 | 80.5 |
| Light impurities (% of the weight of VC) | 1.55 | 1.65 | 1.45 | 1.61 | 1.90 |
| Heavy impurities (% of the weight of VC) | 0.49 | 0.60 | 1.09 | 0.68 | 0.56 |

The D 12 used is a D 12 originating from an industrial unit, containing 99.5% by weight of 1,2-dichloroethane.

EXAMPLE 7

A D 12 cracking operation is carried out under the following conditions and with the following results in an industrial multitube furnace operating at 12 bars (absolute pressure) with an outlet temperature of 500° C.:
Feed:
 D 12 (kmol/h) . . . 276.6
 HCl (kmol/h) . . . 147.7
 Initiator . . . $10^{-3}$ mol/mol of D 12
Cracking ratio:
 Based on D 12 (%) 0.82.6
Selectivity for vinyl chloride 99.23%

By way of comparison, to obtain the same output of vinyl chloride per hour, in a plant operating with the same proportion of initiator but without HCl, the furnace has to be fed with 415.4 kmol/h of D 12 (55% conversion with 99.3% selectivity).

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A process for the preparation of vinyl chloride from 1,2-dichloroethane, comprising (a) continuously introducing a feedstream of 1,2-dichloroethane and HCl into an empty reactor thus obtaining a reactor containing said feedstream, wherein such feedstream the molar ratio of HCl to 1,2-dichloroethane ranges from 0.1 to 1.8, (b) continuously noncatalytically thermally cracking said feedstream into vinyl chloride within said reactor containing said feedstream, in vapor phase, at a temperature ranging from about 300° to 650° C. and under an absolute pressure ranging from 1 to 40 bars, and (c) continuously recovering vinyl chloride, as it is formed, from said reactor containing said feedstream, wherein said process is carried out at a conversion rate of 95% or higher and without carbonaceous build-up.

2. A process for thermally cracking 1,2-dichloroethane to produce vinyl chloride, said process comprising the steps of:

(a) feeding 1,2-dichloroethane and hydrogen chloride into an empty reactor; and (b) thermally cracking said 1,2-dichloroethane in the presence of said hydrogen chloride to form vinyl chloride.

3. A process for cracking 1,2-dichloroethane to produce vinyl chloride, said process comprising the steps of:

(a) feeding 1,2-dichloroethane and hydrogen chloride into a reactor; and (b) heating said 1,2-dichloroethane in the presence of said hydrogen chloride and in the absence of a solid catalyst at conditions effective to crack said 1,2-dichloroethane to vinyl chloride.

4. A process for the preparation of vinyl chloride from 1,2-dichloroethane, consisting essentially of (a) continuously introducing a feedstream of 1,2-dichloroethane and HCl into an empty reactor thus obtaining a reactor containing said feedstream, (b) continuously thermally cracking said feedstream into vinyl chloride within said reactor containing said feedstream, in vapor phase, at a temperature ranging from about 300° to 650° C. and under an absolute pressure ranging from 1 to 40 bars, and (c) continuously recovering vinyl chloride, as it is formed, from said reactor containing said feedstream, wherein said process is carried out at a conversion rate of 95% or higher and without carbonaceous build-up.

5. The process as defined by claim 4, wherein such feedstream the molar ratio of HCl to 1,2-dichloroethane ranges from 0.1 to 1.8.

6. A process for the preparation of vinyl chloride from 1,2-dichloroethane, comprising (a) introducing feedstream of 1,2-dichloroethane and HCl into an empty reactor thus obtaining a reactor containing said feedstream, (b) thermally cracking said feedstream into vinyl chloride within said reactor containing said feedstream, in vapor phase, at a temperature ranging from about 300° to 650° C. and under an absolute pressure ranging from 1 to 40 bars, and (c) recovering vinyl chloride, as it is formed, from said reactor containing said feedstream, wherein said process is carried out at a conversion rate of 95% or higher and without carbonaceous build-up.

7. The process as defined by claim 6, said feedstream further comprising a free radical-generator.

8. The process as defined by claim 7, said free radical-generator comprising $Cl_2$, $CCl_4$ or $C_2Cl_6$.

9. The process as defined by claim 6, wherein such feedstream the molar ratio of HCl to 1,2-dichloroethane ranges from 0.1.to 1.8.

10. The process as defined by claim 6, said empty reactor comprising a multitube furnace.

11. The process as defined by claim 6, said empty reactor comprising a coil furnace.

* * * * *